(12) United States Patent
Graham

(10) Patent No.: US 6,722,878 B2
(45) Date of Patent: Apr. 20, 2004

(54) LINGUAL ARCHWIRE FORMING APPLIANCE

(76) Inventor: Neil John Graham, 6017 Lido La., Long Beach, CA (US) 90803

( * ) Notice: Subject to any disclaimer, the term of this patent is extended or adjusted under 35 U.S.C. 154(b) by 183 days.

(21) Appl. No.: 10/118,696

(22) Filed: Apr. 10, 2002

(65) Prior Publication Data

US 2003/0194676 A1 Oct. 16, 2003

(51) Int. Cl.[7] ................................................. A61C 7/00
(52) U.S. Cl. ................................ 433/3; 433/20; 433/22
(58) Field of Search .............................. 433/3, 10, 15, 433/20, 22

(56) References Cited

U.S. PATENT DOCUMENTS 3,205,577 A * 9/1965 Linde .......................... 433/23
3,916,526 A * 11/1975 Schudy ........................ 433/20
5,017,133 A * 5/1991 Miura ......................... 433/20

OTHER PUBLICATIONS

Sullivan_Schein Dental Merchandise Catalog 2002 Three pages:cover,p. 454, and p. 455. One page: explanation of relevance.

* cited by examiner

Primary Examiner—Cary E. O'Connor
(74) Attorney, Agent, or Firm—Neil John Graham

(57) ABSTRACT

A lingual archwire forming appliance for adapting a wire to the lingual surfaces of a patient's teeth during the construction of a bonded lingual archwire retainer. The appliance is composed of a handle attached to an arch-formed wire. The combination of the handle and curved archwire are useful in fitting a bonded lingual archwire directly in a patient's mouth.

11 Claims, 1 Drawing Sheet

LINGUAL ARCHWIRE FORMING APPLIANCE

FIELD OF THE INVENTION

The present invention relates to a fixed orthodontic wire retainer for maintaining the alignment of the teeth following orthodontic treatment. The appliance is used to form or adapt the wire to fit the teeth during the construction of the retainer.

BACKGROUND OF THE INVENTION

Fixed orthodontic retainers have been used in orthodontics since the early part of the 20th century. To clarify the description of the invention certain dental terms should be understood. Upper and lower teeth are termed maxillary and mandibular teeth, respectively. Front teeth are anterior teeth and back teeth are posterior teeth. Anterior teeth are incisors and are named centrals, laterals, and cuspids in order from midline to posterior. Posterior teeth from anterior to posterior are first and second bicuspids and first, second, and third molars. Individual teeth are described according to their surfaces. The distal surface is towards the back of the mouth and the mesial surface is towards the front of the mouth. The lingual or palatal surface is on the tongue side of the teeth. The labial or buccal surface is on the cheek or lip side of the teeth The occlusal surface of a tooth is its chewing surface.

The orthodontic procedure for maintaining the teeth straight following orthodontic treatment involves a wire bonded to the inner surface of the front teeth, most commonly the lower anterior teeth. The general shape of the wire is that of an arch, but each mouth is different in size, shape, and form of the arch, requiring the preformed wire to be adapted to the lingual surfaces of the anterior teeth. The adaptation process intraorally is difficult; therefore, soft wires have been used which have made the adapting of the wire to the teeth easier, but the soft wire is easily deformed when worn by the patient. Another approach is to fit the wire to a mold of the patient's teeth. The mold method is time consuming as it requires a mold made from an impression of the patient's teeth, the wire fitted to the mold, and an additional visit for the patient to receive the lingual retainer. The fitting of the archwire in a patient's mouth has been difficult because each time the archwire was placed in the mouth the plane of the archwire, in relation to the teeth, would be slightly different, which makes adapting wire to the lingual surfaces of the teeth slow and difficult. The fitting process required the archwire to be repeatedly placed in the s adjusted. The archwire could not be repeatedly placed in the same position in relation to the teeth, making the adapting bends difficult and slow. The premade lingual archwires have usually included orthodontic mesh pads for bonding to the lingual surfaces of the teeth, usually the cuspids. The mesh pads are integral with the archwire, requiring a variety of lengths of premade archwires. One variation of the mesh pads was a universal size where one of the mesh pads was adjustably positioned. The mesh pads increased the difficulty of fitting the archwire to the teeth because the pads must be fitted to the lingual surface the teeth in another dimension which was vertical to the horizontal plane of the arcuate archrire.

SUMMARY OF THE INVENTION

The present invention is directed to a retainer archwire forming apparatus for adapting an archwire to the inner surfaces of the teeth. The archwire, when bonded to the patient's teeth, becomes a fixed lingual retainer which maintains teeth alignment following orthodontic treatment. The archwire forming apparatus consists of an arcuate archwire portion connected to a handle portion. The arcuate archwire portion is formed in the shape of an arch on a single plane, that plane being parallel to the occlusal plane of the teeth when the arcuate archwire is placed in the mouth during the fitting process. The handle portion is connected to the end of the arcuate archwire which corresponds with the left side of the mouth when the arcuate archwire is placed in the mouth. The axis of the handle is parallel to the plane of the arcuate archwire and extends away from the mouth at a 90 degree angle to the point of attachment to the arcuate archwire. The handle at its point of attachment to the arcuate archwire has a bayonet bend. The bayonet bend extends towards the occlusal plane of the teeth four to six millimeters, allowing the body of the handle to clear the teeth during the fitting process of the arcuate archwire portion.

The handle portion of the archwire forming apparatus must have sufficient length to be hand held. The outer portion, or left end, of the handle has a flat area to enhance the grip of the wire. The flat area is parallel to the plane of the arcuate archwire and is formed by placing two successive bends in the wire at the outer end of the handle away from the mouth. The bends are done at an 8 mm interval. The exact dimension or shape of the flat area is not critical, but the dimension must be large enough for the apparatus to the hand held in a stable manner during the fitting process. The flat area would also be useful if it were vertical to the horizontal plane of the arcuate archwire. The object of the invention is the ability to repeatedly place the arcuate archwire into the mouth in the same relative position to the patient's anterior teeth.

The handle portion allows the lingual archwire appliance to be firmly held, allowing the arcuate archwire to be repeatedly positioned in the mouth in an identical manner. The ability to accurately reposition the arcuate archwire allows its adaptation to the teeth to be done easily with accuracy and efficiency.

In an alternative embodiment of the present invention the handle portion can also be comprised of different materials, such as polypropylene or plastics, attached to the arcuate archwire adhesively or mechanically.

In another embodiment of the present invention the handle can be attached to the arcuate archwire which includes orthodontic bonding pads for adhering the wire to the patient's teeth.

DETAILED DESCRIPTION OF THE INVENTION

Figure 1:
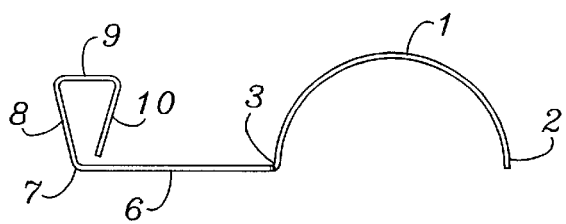
FIG. 1 is a top view of the lingual archwire forming appliance.
Figure 2:
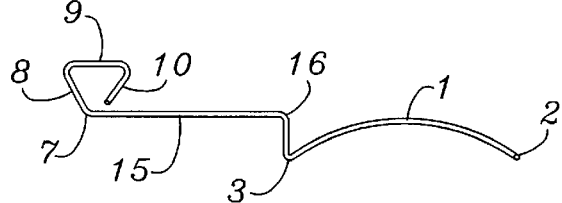
FIG. 2 is a prospective view of the lingual archwire forming appliance.
Figure 3:
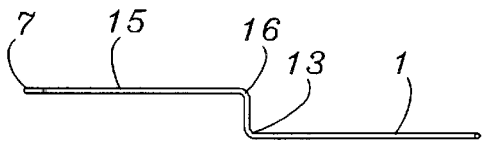
FIG. 3 is a horizontal view of the lingual archwire forming apparatus.

Referring to FIGS. 1–6, the orthodontic archwire forming apparatus has an arcuate archwire 1 formed on a plane FIG.

3. The arcuate archwire 1 is used to form the lingual archwire retainer FIG. 6. Attached to an end of the arcuate archwire 3 is the wire handle 6 extending outwardly from the arcuate archwire 1, the handle axis 15 is 90 degrees to the arcuate archwire at the point of attachment 3 and in the same plane as the planar dimension of the arcuate archwire 1. The length of the handle 6 must be sufficient for the handle 6 to be hand held.

At the outward end of the handle 6 is a horizontal flat area 10 created by bending the wire 7, 8 and 9. The flat area 8 provides stability when the handle is hand held. The ability to hand hold the handle 10 in a stable manner is the important feature of the invention. The arcuate archwire 1 can be easily repeatably placed in the patient's mouth lingual to the anterior teeth, FIG. 6, in the same plane as the occlusal plane. Adjusting the arcuate archwire 1 to fit the patient's teeth requires the arcuate archwire 1 to be repeatedly placed in the patient's mouth. The attached handle FIGS. 1–6 makes it possible to repeatedly return the arcuate archwire 1 to the mouth in the same relative position to the patient's teeth. The curvature of the arcuate archwire 1 should be slightly greater than the lingual anterior tooth curvature 33. During the adaptation of the arcuate archwire 1 to the lingual surfaces of the anterior teeth it is easier to decrease the curvature of a wire than increase the curvature of a wire. The handle 6, at its attachment to the arcuate archwire 1, extends occlusally 13, 16 4–5 mm in order for the handle 6 to clear the teeth when placed in the mouth, as in FIG. 6. A right angle bend 13 extends occlusally and another right angle bend extends the wire away from the arcuate archwire 1.

In the preferred embodiment the handle 6 and arcuate archwire 1 portion are comprised of a continuous wire. The preferred embodiment is 0.028 inch stainless steel wire. The archwire former can be used on models of teeth or in the mouth to form the lingual archwire retainer. The wire can be 0.020 inch diameter to 0.080 inch in diameter. The lingual archwire forming apparatus allows the lingual archwire 1 to be easily formed in the mouth because the handle 6 allows the arcuate archwire 1 to be repeatedly repositioned in the mouth in the same plane and relative position to the patient's teeth.

Figure 6:
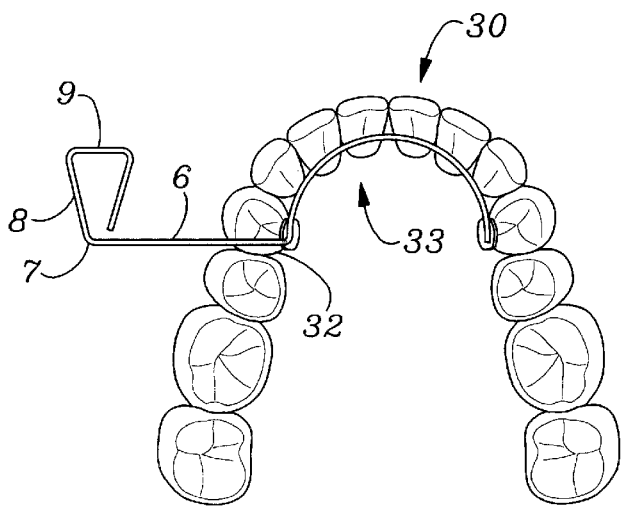
FIG. 6 is a horizontal view of the archwire forming apparatus placed lingual to the lower anterior teeth.

The process of forming the lingual retainer involves the steps of gripping the handle 6 of the apparatus, placing the arcuate portion in the patients mouth adjacent to the lingual of the anterior teeth 30 parallel to the occlusal plane, cutting the approximate length 2, adjusting the curvature to fit the teeth, and adjusting the wire to fit the teeth by repeated adjustments after repeatedly placing the arcuate archwire in the mouth, FIG. 6, in the same relative position. Most importantly, the planar dimension of the arcuate archwire 1 must be repeatably parallel to the occlusal plane. The arcuate archwire is attached to selected teeth by holding the archwire 1 in position and adhesively bonding the arcuate archwire 1 to the teeth 32.

Figure 4:
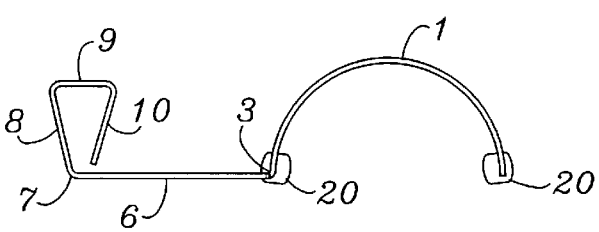
FIG. 4 is a top view of another embodiment of the lingual archwire forming apparatus.
Figure 5:
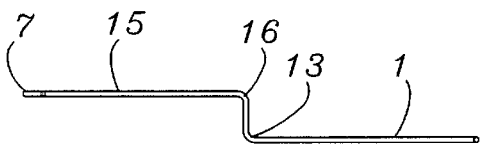
FIG. 5 is a horizontal view of the lingual archwire forming apparatus of FIG. 4.

In another embodiment of the present invention the arcuate archwire 1 has mesh orthodontic pads 20 attached to it as shown in FIGS. 4 and 6. The handle 6 can be attached to the pad 20 or wire, most commonly corresponding to the left side of the patient's mouth, by being continuous with, soldered to, electrowelded to, or adhesively attached to the arcuate archwire 1.

In another embodiment of the orthodontic archwire forming appliance the handle 6 can be a nonmetallic material such as plastic or polypropylene having sufficient rigidity to support the arcuate wire portion during the fitting process to the teeth. The handle 6 can be attached to the arcuate archwire 1 portion adhesively and/or mechanically. The handle 6 can also be used to help adapt removable lingual or palatal arch wires directly in the patient's mouth or a model of the patient's teeth.

In another embodiment of the invention the handle 6 can be attached to a labial wire used in the construction of removable retainers, such as Hawley retainers.

The invention has been described with specific embodiments, however, the intent of the invention is to provide an archwire forming appliance which makes it possible to form a retainer archwire directly in the patient's mouth. The difficulty of forming a lingual archwire retainer in the past has frequently required the use of a study model of the patient's teeth upon which to adapt the wire, which required an impression of the patient's teeth and a subsequent visit to bond the lingual retainer to the patient's teeth. The invention makes it possible to both form the lingual archwire quickly and accurately within the mouth and bond the lingual archwire to the patient's teeth during a single patient visit.

What is claimed:

1. An archwire forming appliance for making an orthodontic lingual archwire retainer comprising:
   a planar arcuate archwire having left and right sides, which correspond with the left and right sides of the patient's mouth when the arcuate wire is placed in a patient's mouth lingual to the patient's anterior teeth, and sufficient in length to extend on the lingual surfaces of the patient's six anterior incisors and first bicuspids; and
   a longitudinal handle attached to the planar arcuate archwire, the handle having a longitudinal body spine with opposing left and right longitudinal ends and a longitudinal axis, the left end of the handle has a flat area extending at a right angle to the handle and parallel to the planar dimension of the arcuate wire, this flat area is of sufficient dimension to allow the handle to be handheld in a stable manner during the fitting of the arcuate wire in the patients mouth, the appliance to be handheld and repositioned repeatedly in the mouth in a similar position during the adaptation of the arcuate wire to the lingual surfaces of the patients teeth, and the longitudinal handle attaches at a right angle to the arcuate archwire and extends towards the patient's occlusal plane a sufficient distance to avoid the teeth when the handle is placed in the mouth.

2. An archwire forming apparatus for adaptably forming a lingual archwire comprising:
   an orthodontic planar arcuate archwire with two ends wherein each end has attached to it an orthodontic mesh pad positioned opposite to and parallel to the lingual surfaces of the teeth the mesh pads are to be bonded to;
   a handle attached to the arcuate archwire or orthodontic mesh pad and extending away from the arcuate archwire, allowing the arcuate archwire to be repeatedly repositioned in a patient's mouth in the same relative position to the patient's anterior teeth during the adaptation process of the arcuate wire to the lingual surfaces of the patient's anterior teeth; and
   a flat area at the end of the handle opposite the arcuate archwire attachment wherein the flat area is parallel to the planar dimension of the arcuate archwire, the flat area allowing the handle to be repeatably held in the same position.

3. An archwire forming apparatus as in claim 2 wherein the arcuate archwire and handle are 0.020 inch diameter to 0.080 inch diameter wire.

4. An archwire forming apparatus as the claim 2 wherein the arcuate archwire and handle are 0.028 inch diameter wire.

5. An archwire forming apparatus as in claim 2 wherein the handle is parallel to the planar dimension of the arcuate archwire.

6. An archwire forming apparatus as in claim 2 wherein the flat area of the handle is at a right angle to the planar dimension of the arcuate archwire.

7. An archwire forming apparatus as in claim 2 wherein the end of the handle opposite the flat area is attached to the right end of the arcuate archwire, allowing a left-handed person to hold the handle with the right hand, leaving the left hand free to bend the arcuate archwire.

8. An archwire forming apparatus as in claim 2 wherein the end of the handle opposite the flat area is attached to the arcuate archwire in any position between the left and right ends of the arcuate archwire.

9. An archwire forming apparatus as in claim 2 wherein the handle is attached to an arcuate archwire with loops which is repeatedly adaptively positioned to the labial surface of the anterior teeth of a model of teeth to form a labial wire for a removable retainer, such as a Hawley retainer.

10. A method of forming a bonded lingual archwire comprising the steps of:

holding the archwire forming appliance by the handle;

placing the arcuate archwire of the appliance in the patient's mouth, the arcuate curve against the lingual surfaces of the patient's anterior teeth;

positioning the arcuate archwire in the mouth with the planar dimension of the arcuate archwire parallel to the occlusal plane of the patient's teeth;

bending the arcuate archwire to conform to the lingual surfaces of the anterior teeth;

positioning the arcuate archwire repeatedly in the same position in the mouth and repeatedly bending the wire to fit the lingual surfaces of the anterior teeth;

cutting the right end of the arcuate archwire length to conform with the number of teeth to be retained by the lingual archwire;

placing the arcuate archwire against the lingual surfaces of the anterior teeth; and bonding the arcuate archwire to the teeth.

11. A method of forming a bonded lingual archwire as in claim 10 wherein the act of forming the arcuate archwire to fit the patient's teeth is performed by fitting the arcuate archwire upon a model of the patient's teeth.

\* \* \* \* \*